(12) United States Patent
Anglin, Jr. et al.

(10) Patent No.: US 9,011,779 B1
(45) Date of Patent: Apr. 21, 2015

(54) DEVICE FOR MEASUREMENT OF EXHALED ETHANOL CONCENTRATION

(71) Applicant: Andas, Inc., Minneapolis, MN (US)

(72) Inventors: Timothy Clay Anglin, Jr., Durham, NC (US); Timothy D. Berner, New York, NY (US); Joseph C. Jensen, Minneapolis, MN (US)

(73) Assignee: Andas Inc., Minneapolis, MN (US)

( * ) Notice: Subject to any disclaimer, the term of this patent is extended or adjusted under 35 U.S.C. 154(b) by 0 days.

(21) Appl. No.: 14/334,853

(22) Filed: Jul. 18, 2014

Related U.S. Application Data

(63) Continuation-in-part of application No. 14/283,798, filed on May 21, 2014.

(51) Int. Cl.
| | |
|---|---|
| *H01L 29/93* | (2006.01) |
| *H01L 29/00* | (2006.01) |
| *G01N 27/22* | (2006.01) |
| *G01N 27/00* | (2006.01) |
| *G01N 33/98* | (2006.01) |

(52) U.S. Cl.
CPC .............. *G01N 33/98* (2013.01); *Y10S 977/734* (2013.01); *Y10S 977/735* (2013.01); *Y10S 977/737* (2013.01); *Y10S 977/738* (2013.01); *Y10S 977/74* (2013.01)

(58) Field of Classification Search
USPC ................ 422/68.1, 82.01, 82.02, 83, 84, 98; 73/23.2, 23.3, 31.05, 31.06; 438/48, 438/49; 977/734, 735, 737, 738, 740
See application file for complete search history.

(56) References Cited

U.S. PATENT DOCUMENTS

| | | | |
|---|---|---|---|
| 5,447,165 | A | 9/1995 | Gustafsson |
| 5,565,075 | A | 10/1996 | Davis |
| 5,795,787 | A | 8/1998 | Silkoff |
| 6,287,452 | B1 | 9/2001 | Allen |
| 6,612,306 | B1 | 9/2003 | Mault |

(Continued)

FOREIGN PATENT DOCUMENTS

| | | |
|---|---|---|
| WO | 2007136523 | 11/2007 |
| WO | 2012145247 | 10/2012 |
| WO | 2012145247 A1 | 10/2012 |

OTHER PUBLICATIONS

Shan Jiang, Rui Cheng, Xiang Wang, Teng Xue, Yuan Liu, Andre Nel, Yu Huang, Xiangfeng Duan; Real-time electrical detection of nitric oxide in biological systems with sub-nanomolar sensitivity; Nature Communications, 2013, 4, 2225. (Jul. 26, 2013).

(Continued)

*Primary Examiner* — In Suk Bullock
*Assistant Examiner* — Robert Eom
(74) *Attorney, Agent, or Firm* — McDonnell Boehnen Hulbert & Berghoff LLP

(57) ABSTRACT

Described is a personal device and methods for measuring the concentration of an analyte in a sample of gas. The device and method may utilize a chemically selective sensor element with low power consumption integrated with circuitry that enables wireless communication between the sensor and any suitable electronic readout such as a smartphone, tablet, or computer. In preferred form, the sensor circuitry relies upon the quantum capacitance effect of graphene as a transduction mechanism. Also in preferred form, the device and method employ the functionalization of the graphene-based sensor to determine the concentration of ethanol in exhaled breath.

20 Claims, 6 Drawing Sheets

(56) References Cited

U.S. PATENT DOCUMENTS

| | | |
|---|---|---|
| 7,914,664 B2 | 3/2011 | Bayachou |
| 2006/0193749 A1 | 8/2006 | Ghazarian |
| 2009/0054799 A1 | 2/2009 | Vrtis |
| 2010/0137733 A1 | 6/2010 | Wang |
| 2011/0098591 A1 | 4/2011 | Haick |
| 2011/0239735 A1 | 10/2011 | Setayesh |
| 2012/0058350 A1 | 3/2012 | Long |
| 2013/0334579 A1 | 12/2013 | Accardi |

OTHER PUBLICATIONS

Steven J. Koester, "High quality factor graphene varactors for wireless sensing applications"; Applied Physics Letters, 2011, 99, 163105 (Oct. 18, 2011).

Rodenstein, D.O., Stanescu, D.C., Absence of nasal air flow during pursed lips breathing. The soft palate mechanisms. Am. Rev. Respir. Dis. Oct. 1983; 128(4), 716-718.

Philip E. Silkoff, Patricia A. McClean, Arthur S. Slutsky, Henry G. Furlott, Eric Hoffstein, Suguru Wakita, Kenneth R. Chapman, John P. Szalai, and Noe Zamel; "Marked Flow-dependence of Exhaled Nitric Oxide Using a New Technique to Exclude Nasal Nitric Oxide"; Am J Respir Crit Care Med 1997; 155:260-267. (Jan. 1997).

ATS/ERS Recommendations for Standardized Procedures for the Online and Offline Measurement of Exhaled Lower Respiratory Nitric Oxide and Nasal Nitric Oxide, 2005; American Thoracic Society Documents, Am J Respir Crit Care Med 2005; 171:912-930. (Apr. 15, 2005).

K. Ichimori, H. Ishida, M. Fukahori, H. Nakazawa, and E. Murakami; Rev. Sci. Instrunn. 65, 2714 (1994); doi: 10.1063/1.1144674 (Aug. 1994).

Fei Liu, Ki Seok Choi, Tae Jung Park, Sang Yup Lee & Tae Seok Seo; "Graphene-based electrochemical biosensor for pathogenic virus detection"; BioChip J. (2011) 5(2): 123-128 (Jun. 20, 2011).

M. Lazarova, P. Bosch, and A. Friedl; "POMS Membrane for Selective Separation of Ethanol from Dilute Alcohol-Aqueous Solutions by Pervaporation"; Separation Science and Technology, 47: 1709-1714, 2012 (Aug. 7, 2012).

Hahn, R. G., Jones, A. W., Billing, B., Stalberg, H. P.; "Expired-breath ethanol measurement in chronic obstructive pulmonary disease: implications for transurethral surgery"; Acta Anaesthesia! Scand. Jul. 1991;35(5):393-7.

Pietro R. Galassetti, M.D., Ph.D., Brian Novak, B.S., Dan Nemet, M.D., Christie Rose-Gottron, M.S., Dan M. Cooper, M.D., Simone Meinardi, Ph.D., Robert Newcomb, Ph.D., Frank Zaldivar, Ph.D., and Donald R. Blake, Ph.D.; "Breath Ethanol and Acetone as Indicators of Serum Glucose Levels: An Initial Report"; Diabetes Technology & Therapeutics vol. 7, No. 1, 2005, 115-123 (Feb. 2005).

Kechagias S, Jonsson K-Å, Franzén T, Andersson L, Jones AW. Reliability of breath-alcohol analysis in individuals with gastroesophageal reflux disease. J Forensic Sci 1999;44(4): 814-818 (Nov. 1999).

DEVICE FOR MEASUREMENT OF EXHALED ETHANOL CONCENTRATION

BACKGROUND

The present invention is in the technical field of analyte sensors. More particularly, the present invention is in the field of exhaled breath chemical sensors. In preferred form, the present invention is in the field of nitric oxide breath sensors. In other preferred embodiments, the invention provides a method and device for measuring the concentration of ethanol in exhaled breath.

Electronic circuits that utilize organic materials, such as graphene, have been explored for their potential use in electrochemical sensors. The attraction to using such compounds is the ability to chemically modify the organic materials to introduce new functionality by, for example, attaching a receptor molecule that sensitizes the device toward a particular analyte.

Many sensors have been conceived that utilize graphene in transistor or resistive circuits for the purpose of sensing. However, it is only recently that the ability to use graphene in a variable capacitor device was demonstrated. Although a graphene variable capacitor design has some advantages for use in breath diagnostic sensing, the graphene varactor itself may not be selective toward any particular compound and may be compromised in its ability to discriminate between the target analyte and interfering compounds.

SUMMARY

In one aspect, this disclosure provides a device for measuring the concentration of an analyte in exhaled breath. The device may consist of one or more analyte sensor circuits including an analyte sensor, power supply, and wireless transmitter (e.g. Bluetooth) for communicating the concentration of the analyte to a personal electronic device for readout and display, interpretation, or other action.

In some embodiments, the analyte sensor in the device may be a modified graphene variable capacitor (varactor). The varactor may include a modifying layer that specifically binds to an analyte. The binding of the analyte may alter the local electrostatics at the graphene surface and can cause a shift in the quantum capacitance of the graphene in the varactor device. This change in capacitance may be read by additional circuit elements in the device. One method for determining the change in capacitance may be to measure the shift in resonant frequency of a wireless resonator. The resonator may comprise an inductor and the graphene capacitor. This method may be relatively immune to thermal variation, environmental variation, or changes in varactor resistance.

In another aspect, this disclosure provides a method and device for measuring the concentration of an analyte in exhaled breath. In a preferred embodiment, invention provides a method and device for measuring the concentration of nitric oxide in exhaled breath. In other preferred embodiments, the invention provides a method and device for measuring the concentration of ethanol in exhaled breath. Data may be collected when a user exhales into a device having a modified graphene variable capacitor (varactor). The data obtained by the sensor may be used to inform medical treatment, refine therapeutic strategies, or collect data to aid in the diagnosis of respiratory diseases or other conditions for which the analyte measured is an indicator. The data obtained may also be used for personal monitoring of breath analyte concentration for the purpose of determining blood analyte concentration. In some embodiments, the device may be used in conjunction with vehicle interlock systems, compliance monitoring, workplace safety screening, etc.

DETAILED DESCRIPTION

Figure 1:
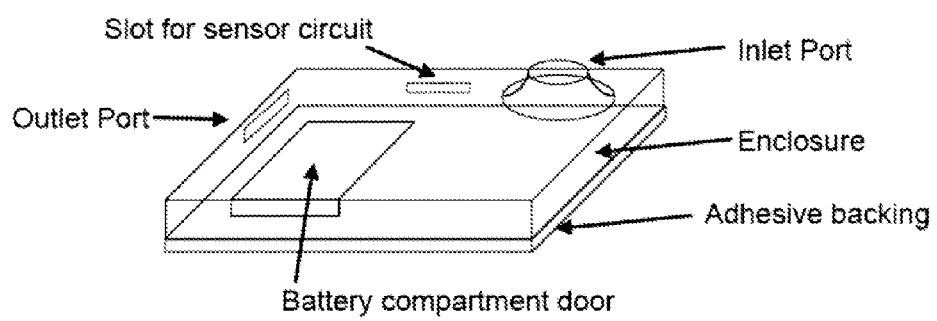
FIG. 1 is device according to an example embodiment. View (A) shows the external elements of the device and (B) shows the major internal components as viewed from top.
Figure 1:
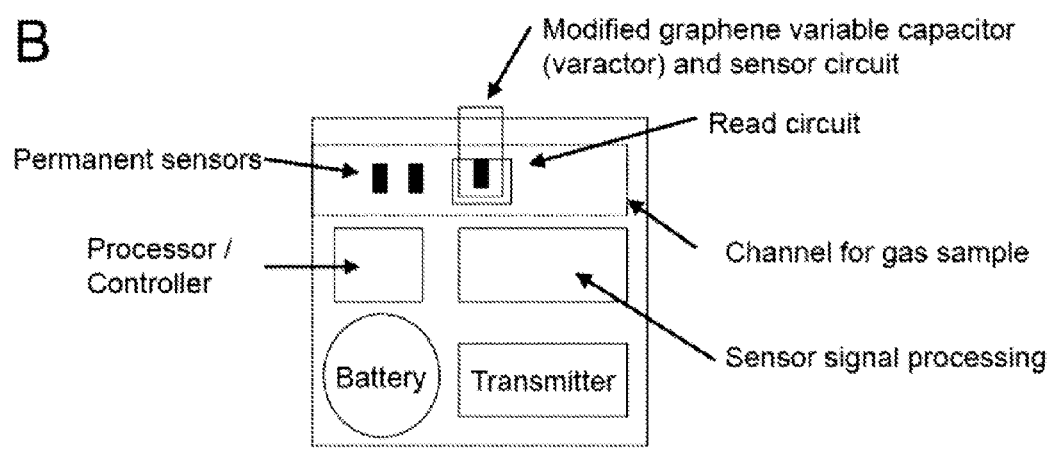
Figure 2:
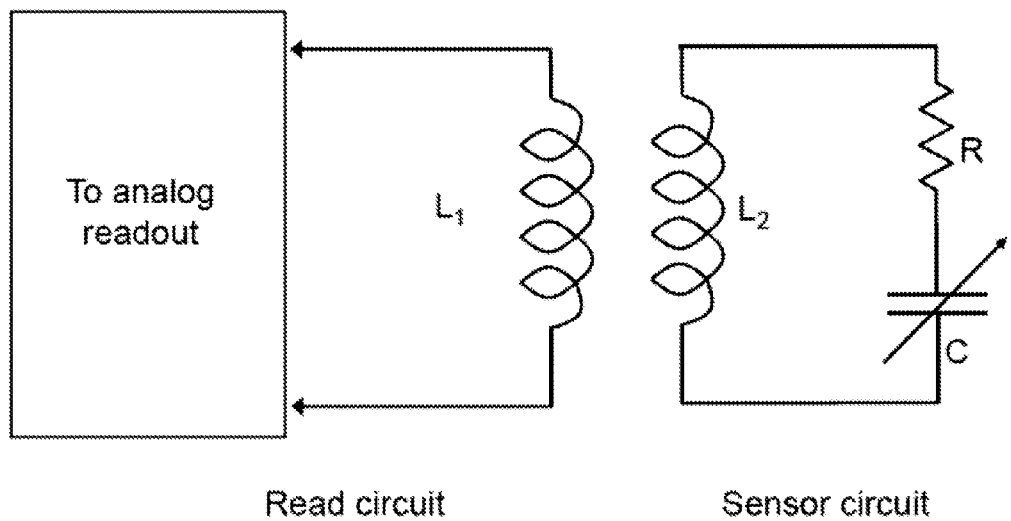
FIG. 2 is a read circuit and a sensor circuit according to an example embodiment. The sensor circuit includes a modified graphene variable capacitor (varactor) (C), having some series resistance (R), and is coupled to a sensor inductor ($L_2$). The sense inductor is inductively coupled to a nearby read inductor ($L_1$) that is part of the analog readout circuit (read circuit) used to measure change in capacitance of the graphene varactor (C).
Figure 3:
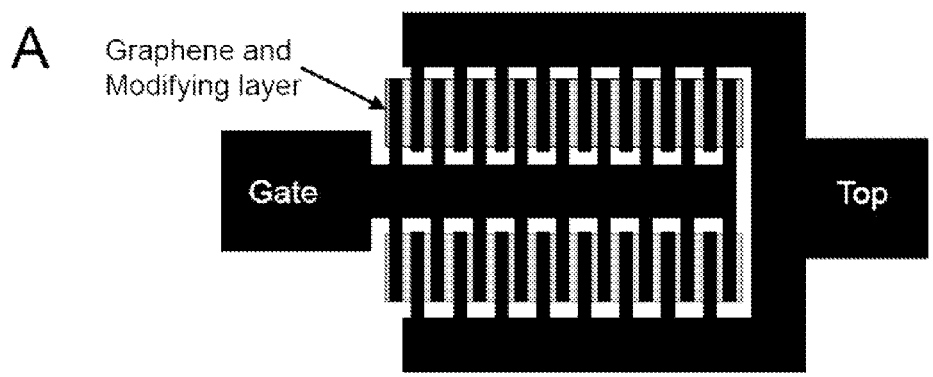
FIG. 3 is a multi-finger graphene varactor geometry with modified sensing layer according to an example embodiment. The graphene varactor sensor geometry is shown with top view (A) and cross sectional view (B). The graphene layer is shown in grey
Figure 3:
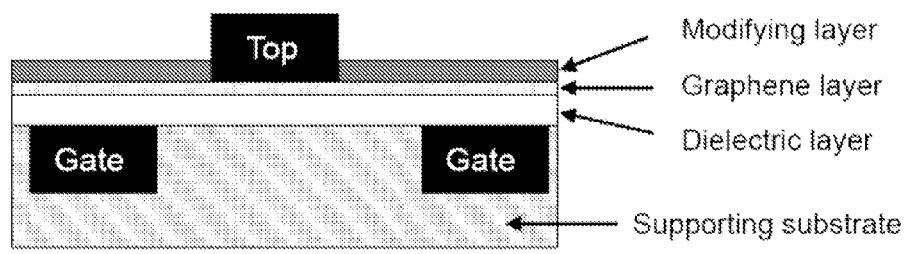
Figure 4:
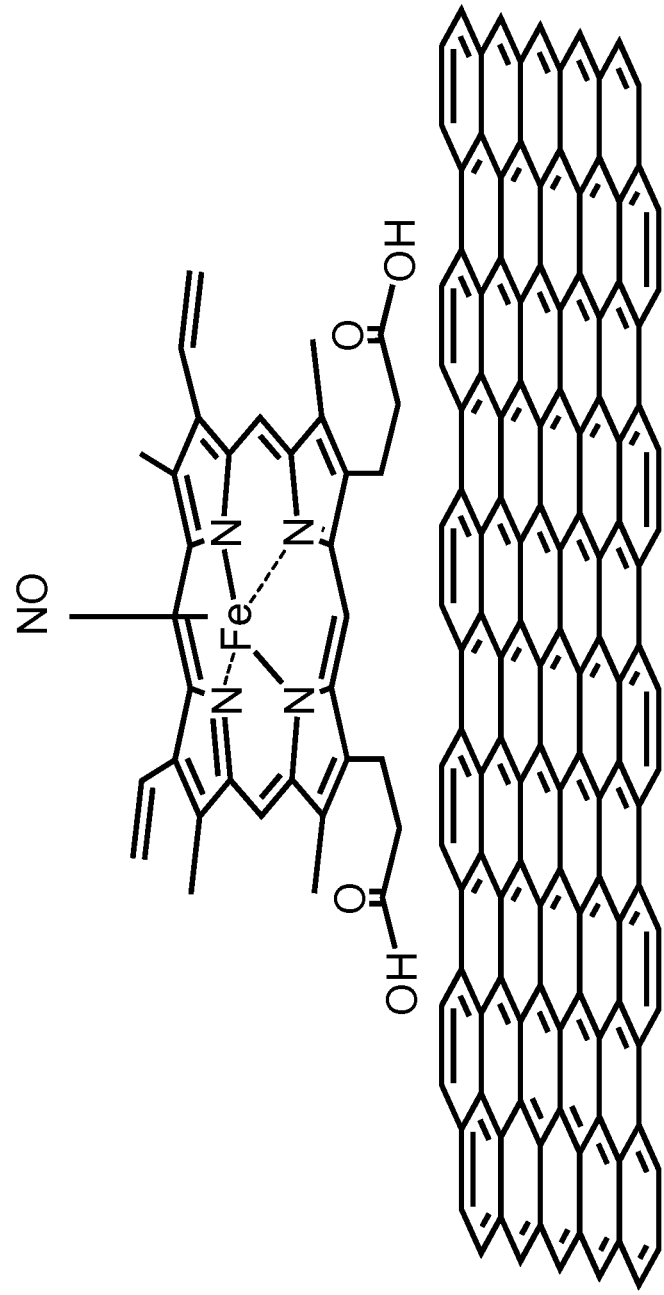
FIG. 4 is an example of non-covalent modification of graphene with hemin chloride according to an example embodiment.
Figure 5:
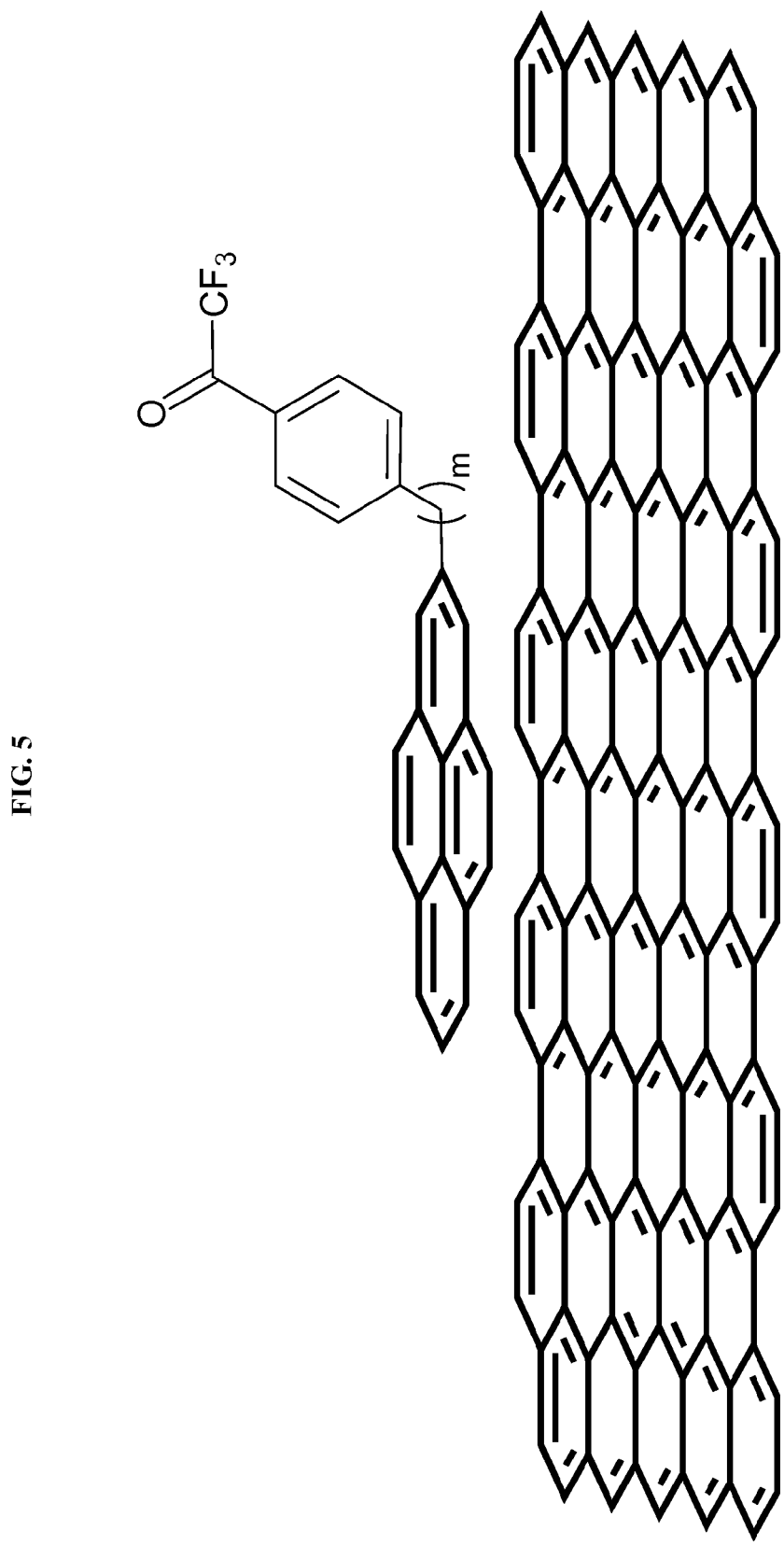
FIG. 5 is an example of non-covalent modification of graphene with a pyrene-substituted trifluoroacetate moiety according to an example embodiment.
Figure 6:
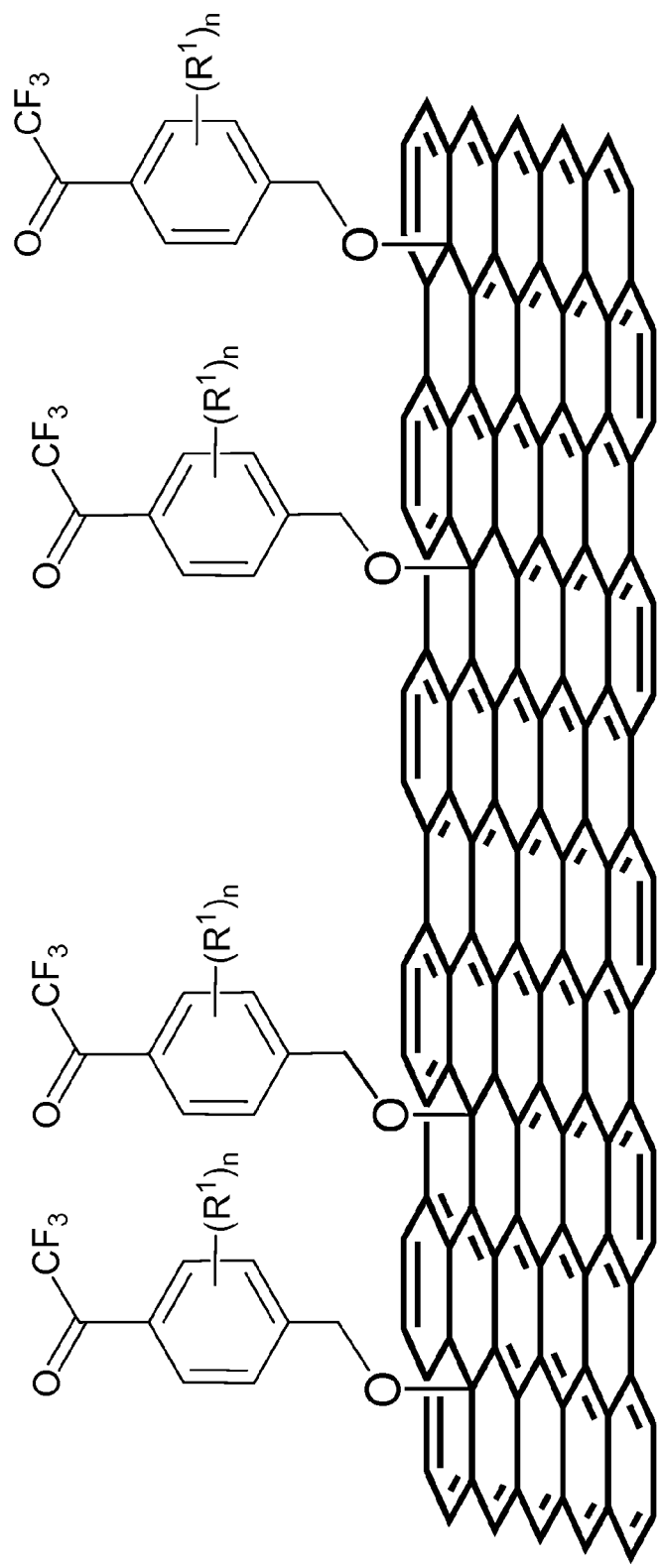
FIG. 6 is an example of covalent modification of graphene with a trifluoroacetate moiety according to an example embodiment.

The following detailed description describes various features and functions of the disclosed devices and methods with reference to the accompanying figures. In the figures, similar symbols typically identify similar components, unless context dictates otherwise. The illustrative device and method embodiments described herein are not meant to be limiting. It will be readily understood that certain aspects of the disclosed devices and methods can be arranged and combined in a wide variety of different configurations, all of which are contemplated herein.

I. Definitions

The term "alkyl" as used herein, refers to a straight or branched chain hydrocarbon moiety containing from 1 to 12 carbon atoms and generally having the formula $C_nH_{2n+1}$, unless otherwise specified. Representative examples of alkyl groups include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "$C_1$-$C_{20}$alkyl" as used herein, refers to a straight or branched chain hydrocarbon moiety containing from 1 to 20 carbon atoms and generally having the formula $C_nH_{2n+1}$, unless otherwise specified. Representative examples of alkyl groups include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When a $C_1$-$C_{20}$alkyl is used as a divalent radical, it generally has the formula $C_nH_{2n}$.

The term "alkenyl" as used herein, means a straight or branched chain hydrocarbon moiety containing from 2 to 12 carbons, unless otherwise specified, and containing at least one carbon-carbon double bond. Representative examples of alkenyl groups include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "$C_1$-$C_{20}$alkenyl" as used herein, means a straight or branched chain hydrocarbon moiety containing from 2 to 20 carbons, unless otherwise specified, and containing at least one carbon-carbon double bond. Representative examples of alkenyl groups include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "aryl" as used herein, means an aromatic six- to fourteen-membered carbocyclic ring, for example, benzene, pyrene, naphthalene, anthracene, indane, tetralin, fluorene and the like. As univalent radicals, the aforementioned ring examples are named phenyl, pyrenyl, naphthyl, anthracenyl, indanyl, tetralinyl, and fluorenyl.

The term "heteroaryl" as used herein, means an aromatic six- to fourteen-membered ring radical which consists of carbon atoms and from one to five heteroatoms selected from the group consisting of nitrogen, oxygen and sulfur.

The term "$C_1$-$C_{20}$alkyl-aryl" as used herein, means a residue in which an aryl moiety is attached to a parent structure via a $C_1$-$C_{20}$alkyl divalent radical.

The term "$C_1$-$C_{20}$alkyl-heteroaryl" as used herein, means a residue in which a heteroaryl moiety is attached to a parent structure via a $C_1$-$C_{20}$alkyl divalent radical.

The term "optionally" as used herein, means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example, the term "optionally substituted $C_1$-$C_{20}$alkyl-aryl," means that optional substitution may occur on both the "$C_1$-$C_{20}$alkyl" portion and the "aryl" portion of the molecule.

The term "halogen" as used herein, means —F, —Cl, —Br, —I or —At.

The term "transition metal" as used herein, means an element whose atom has a partially filled d sub-shell, or which can give rise to cations with an incomplete d sub-shell. "Transition metals" are included in the d-block of the periodic table, which includes groups 3 to 12 on the periodic table. For example, a "transition metal" may be Sc, Ti, V, Cr, Mn, Fe, Co, Ni, Cu, Pb, Zn Co, Mo, Ru, Rh, Pd, Ag, Os, Ir or Pt.

The term "porphyrin" as used herein, means an aromatic heterocyclic macrocycle composed of four modified pyrrole subunits interconnected at their a carbon atoms via methine bridges (=CH—). Metalloporphyrins have a metal ion coordinated to the porphyrin ring through the pyrrole nitrogen atoms.

I. Devices

In one aspect, the invention provides a device for determining the concentration of an analyte in a volume of gas. The device may include a case with integrated inlet and outlet ports for passing gas over one or more internal sensors. Internal components of the device may include, but are not limited to, one or more analyte sensor circuits, electrical hardware for readout of the sensor circuit(s), and wireless communication hardware for transmitting the data to an external unit for analysis. The sensor circuit may be user-replaceable to enable replacement of a device that has stopped functioning or to introduce a sensor circuit for a different analyte. Other internal components may include additional sensors for pressure, gas flow rate, temperature, humidity, ambient analyte concentration and/or other vapor analytes, which may be located within the same interior space as the sensor circuit. Other internal communication equipment may also be included in the device in order to provide data connectivity between the device and external hardware such as a wireless router, wired Ethernet connection, Bluetooth receiver, or a combination thereof.

In one embodiment, a device for detecting an analyte is disclosed, the device comprising:

one or more analyte sensors, each comprising a graphene-based variable capacitor; and a wireless transmitter, wherein the graphene-based variable capacitor comprises a graphene layer and a modifying layer in contact with the graphene layer.

In some embodiments, the wireless transmitter may enable the device to be used in conjunction with a personal electronic device (PED). The wireless transmitter may be capable of transmitting information by radio, free-space optical, infrared, wireless, USB, Bluetooth or electromagnetic induction. Examples of suitable personal electronic devices include, but are not limited to, a computer, tablet, smartphone or wearable electronic device, such as a watch or head mountable display.

In some embodiments, the device may also include a power supply. In some instances, the device is powered by a personal electronic device used in conjunction with the device. In other embodiments, the device may include means for providing power to the varactor. Means for providing power may be within the device. The device may be powered by battery or through wired connection to an alternating current (AC) or direct current (DC) source. The battery may be rechargeable. Means for providing power may be external to the device. The device may be powered by a PED through a wire or wirelessly, solar power, electricity provided by mechanical energy, including but not limited to a wind generator, manual crank or pull cord or shaking generator, by potential energy, such as device that produces energy from gravity, by thermoelectric or supercapacitor power sources.

In some embodiments, the sensor circuit may include a modified graphene-based variable capacitor (varactor). The interaction between the varactor and an analyte may alter the capacitance of the varactor, providing a quantitative signal. The varactor may include a multi-finger, planarized electrode geometry including a gate electrode and a top electrode (FIG. 1A). In some embodiments, the gate electrode can be embedded in a supporting substrate. A dielectric layer may substantially cover the gate electrode and substrate, and a graphene layer may substantially cover the dielectric layer. The top electrode may be in contact with the surface of the graphene layer opposite to the dielectric layer (FIG. 1B).

In some embodiments, the sensor further includes an insulating layer between the gate electrode and the graphene layer. The insulating layer may be any high dielectric constant material known in the art. The material of the insulating layer may have a relative dielectric constant (K) of about 3.9 or greater. In some embodiments, the K is between about 3.9 and about 25, or between about 5 and about 20, or about 10 and about 20, or about 15 and about 25, or about 10 and about 15, or about 20 and about 30. For example, the insulating layer may comprise $HfO_2$, $Al_2O_3$, or $ZrO_2$.

In some embodiments, the sensor further includes a permeable membrane substantially covering the modifying layer. The permeable membrane may be chosen to selectively allow the analyte being detected to pass through to the modifying layer while limiting the permeability of species not being detected (interferents). The properties of the permeable membrane can be adjusted by altering the composition of the permeable membrane. For example, the permeable layer may be a polymer. In some examples the permeable layer includes a nitrocellulose polymer. In some examples, the permeable layer may be a material with low water permeability, such as poly-alkyl siloxanes. In embodiments where the analyte is ethanol, suitable poly-alkylsiloxanes include those that selectively transport ethanol, particularly in the presence of water and/or acetone. Examples include, but are not limited to poly (dimethylsiloxane) (PDMS) and poly(octylmethylsiloxane) (POMS).

In other embodiments, the modifying layer may also serve as a permeable membrane. For example, the modifying layer can further comprise materials that alter its permeability for a specific analyte. These materials, referred to herein as permeability modifier(s), can be those described as suitable for the permeable membrane. For example, the permeability modifier may include a nitrocellulose polymer. In some embodiments, the modifying layer may include a porphyrin and a permeability modifier. The ratio of permeability modifier to porphyrin may range from about 99:1 to about 30:70. In other embodiments, the ratio of permeability modifier to porphyrin may range from about 90:10 to about 30:70, about 80:20 to about 50:50, about 90:10 to about 60:40, 30:70 to about 70:30, about 90:10 to about 80:20, about 50:50 to about 30:70, about 99:1 to about 50:50, about 40:60 to about 60:40, or about 50:50 to about 30:70.

In other embodiments, the modifying layer may include a trifluoroacetate moiety and a permeability modifier. The ratio of permeability modifier to trifluoroacetate moiety may range from about 99:1 to about 30:70. In other embodiments, the ratio of permeability modifier to trifluoroacetate moiety may range from about 90:10 to about 30:70, about 80:20 to about 50:50, about 90:10 to about 60:40, 30:70 to about 70:30, about 90:10 to about 80:20, about 50:50 to about 30:70, about 99:1 to about 50:50, about 40:60 to about 60:40, or about 50:50 to about 30:70.

In some embodiments, the gate electrode may have a multi-finger, planarized geometry, and the top electrode may utilize a multi-finger geometry, which may provide low resistance and high capacitance for the sensor circuit to facilitate determination of the change in capacitance of the graphene layer (Koester, S. J., *Applied Physics Letters*, 2011, 99, 163105).

In some embodiments, the gate electrode can be embedded in a supporting substrate. The supporting substrate may be any insulating material know in the art. Suitable examples include silicon dioxide, quartz, glass and aluminum oxide. In some embodiments, the supporting substrate comprises materials as described for the insulating layer. In some embodiment, the supporting substrate may also include the use of flexible substrates so that the resulting supporting substrate is flexible.

In some embodiments, the device includes a modifying layer capable of interacting with an analyte. The modifying layer may include molecules that are non-covalently bound to the surface of the graphene in order to preserve the sp2 hybridized carbon-carbon network of the graphene layer, thereby maintaining the high charge mobility and low resistivity of the graphene layer. Alternatively, the modifying layer may be covalently bound to the surface of the graphene layer. In embodiments where the modifying layer is covalently bound to the graphene layer, the number of non-sp2 hybridized sites may be a small fraction of total carbon atoms in the graphene layer in order to maintain low resistivity in the graphene layer. In some embodiments, less than about 10% of the total carbon atoms are non-sp2 hybridized.

In some embodiments, the modifying layer includes a porphyrin. The porphyrin may include a metalloporphyrin, the metal ion of which may be coordinated to the porphyrin ring and can act to bind an analyte as part of the analyte sensing mechanism. The metal ion may include an ion of any "transition metal." For example, the metallocene may include a Sc, Ti, V, Cr, Mn, Fe, Co, Ni, Cu, Pb, Zn Co, Mo, Ru, Rh, Pd, Ag, Os, Ir or Pt metal ion. In some examples, hemin, an iron-based porphyrin derivative, may be used to bind an analyte via the central iron atom.

The porphyrin may be non-covalently bound to the graphene surface via π-stacking interactions. The π-stacking interactions between planar moieties such as a porphyrin ring and the graphene surface can drive self-assembly of the planar molecules onto the surface of the graphene. For example, hemin can be adsorbed to the graphene surface. Different chemical substitution patterns can be used on the periphery of the porphyrin ring, as can different metal substituents.

In other embodiments, the porphyrin may be covalently bound to the graphene surface. The porphyrin may be bound to the graphene surface by a covalent bond connecting a non-sp2 hybridized carbon on the graphene surface with any suitable attachment point on the porphyrin structure. In some embodiments, the modifying layer is covalently bound to the graphene surface though oxygen atoms on the graphene surface. In some embodiments, the minimum number of covalent connections required to keep the modifying layer covalently attached while not disrupting the capacitance of graphene layer is desirable.

In some embodiments, planar functional groups other than porphyrins may be used to accomplish the non-covalent modification of the graphene. For example, the porphyrin moieties can readily incorporate transition metal ions that have good binding affinity for a particular analyte. Other planar moieties, such as pyrene, naphthalene, or other macrocycles, can be employed for non-covalent modification of the graphene sheet in a similar fashion to the porphyrin species. These macrocycles can incorporate transition metal ions capable of binding an analyte.

In some embodiments, the modifying layer comprises molecules of Formula (I):

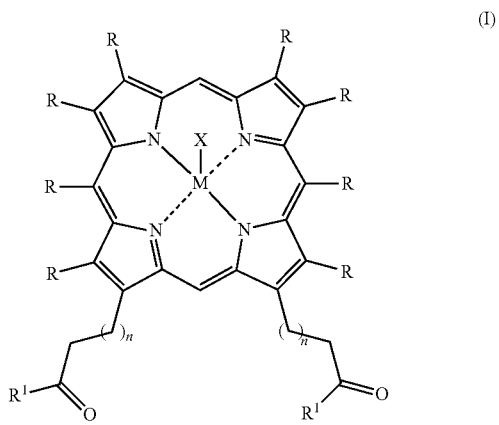

wherein
n is 0, 1, 2, 3, 4, 5, 6, 7, 8, 9 or 10;
each R is independently H, $C_1$-$C_{10}$alkyl, $C_1$-$C_{10}$alkenyl or phenyl;
each $R^1$ is independently —H, —OH, —$NR_2$, $C_1$-$C_{10}$alkyl, —O—$C_1$-$C_{10}$alkyl, -G, —O-G, —N(R)-G, —$C_1$-$C_{10}$alkyl-G or —O—$C_1$-$C_{10}$alkyl-G, wherein G is the graphene layer;
M is a metal; and
X is halogen or cyano.

In some embodiments, the modifying layer comprises molecules of Formula (Ia):

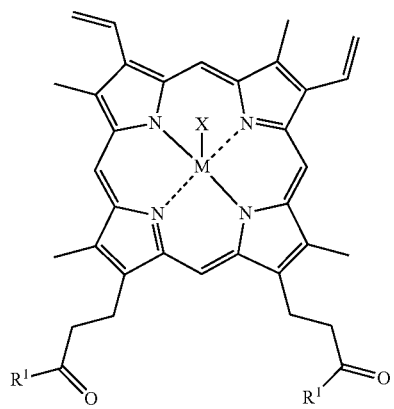

(Ia)

wherein
each $R^1$ is independently —H, —OH, —$NR_2$, $C_1$-$C_{10}$alkyl, —O—$C_1$-$C_{10}$alkyl, -G, —O-G, —N(R)-G, —$C_1$-$C_{10}$alkyl-G or —O—$C_1$-$C_{10}$alkyl-G, wherein G is the graphene layer;
M is a transition metal; and
X is halogen or cyano.

In some embodiments, each R is independently H, $C_1$-$C_{10}$alkyl or $C_1$-$C_{10}$alkenyl. In some instances, —$C_1$-$C_{10}$alkyl can be methyl or ethyl, propyl or isopropyl. $C_1$-$C_{10}$alkenyl can be ethylene, propylene or butylene. In certain embodiments, $C_1$-$C_{10}$alkyl can be methyl and $C_1$-$C_{10}$alkenyl can be ethylene.

In embodiments where the modifying layer is non-covalently bound to the graphene layer, each $R^1$ can be independently —H, —OH, —$NR_2$, $C_1$-$C_{10}$alkyl or —O—$C_1$-$C_{10}$alkyl. In certain embodiments, $R^1$ is —OH.

In embodiments where the modifying layer is covalently bound to the graphene layer, each $R^1$ can be independently -G, —O-G, —N(R)-G, —$C_1$-$C_{10}$alkyl-G or —O—$C_1$-$C_{10}$alkyl-G, wherein G is the graphene layer. In specific examples, $R^1$ is —O-G.

In some embodiments, M can be a transition metal. In certain embodiments, M can be Sc, Ti, V, Cr, Mn, Fe, Co, Ni, Cu, Pb or Zn.

In some embodiments, X can be halogen or cyano. In certain embodiments, X can be chloro, bromo, iodo or cyano. In specific examples, X can be chloro.

In some embodiments, the modifying layer comprises molecules of Formula (Ib):

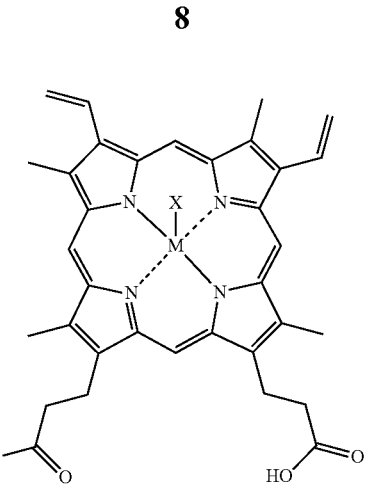

(Ib)

wherein
M is a transition metal; and
X is halogen or cyano.

In some embodiments, the modifying layer includes heme. Suitable types of heme include, but are not limited to, heme A, heme B, heme C, heme O and hemin.

In some embodiments, the interaction of an analyte with the modifying layer and/or graphene layer may cause a change in the local electrostatics (local charge density) and induces a shift in the capacitance of the graphene layer. The modifying layer may also serve to limit the impact of interfering chemical species on the response of the sensor (limits change in capacitance due to other species).

In some embodiments, in addition to non-covalent functionalization of the graphene layer with a modifying layer, the sensor may also include a permeable polymer membrane. The permeable polymer membrane may enhance the selectivity of the sensor toward an analyte.

In some embodiments, the modified graphene varactor sensor may be integrated into a sensor circuit that includes an inductor with precisely known inductance. The circuit consisting of inductor and capacitor may form an inductively coupled resonator whose resonant frequency depends on the capacitance and inductance for the circuit. The capacitance of the sensing element may change in response to the analyte, the resonant frequency may shift accordingly. The resonant frequency of the sensor circuit may be determined using an analog readout circuit that may be paired to the sensor using inductive coupling between the sensor inductor and an inductor in the read circuit.

In some embodiments, the device is a nitric oxide sensor. The graphene varactor may include a modifying layer capable of selectively interacting with nitric oxide. The modifying layer may include molecules that are covalently or non-covalently bound to the graphene surface. Examples of these molecules include metalloporphyrins with good binding affinity for nitric oxide. Hemin, such as hemin chloride, an iron-based porphyrin derivative, is an example of a metalloporphyrin species that can strongly bind nitric oxide via the central iron atom.

In some embodiments, metal ions coordinated by the porphyrin ring can act to bind nitric oxide as part of the sensing mechanism. Hemin, an iron-based porphyrin derivative, can be adsorbed to the graphene surface and bind nitric oxide.

Different chemical substitution patterns can be used on the periphery of the porphyrin ring, as can different metal substituents. Planar functional groups other than porphyrins may be used to accomplish the non-covalent modification of the graphene. In some embodiments, the modifying layer includes a metalloporphyrin of Formula I.

In some embodiments, the planar porphyrin moieties can be non-covalently bound to the graphene surface via π-stacking interactions. The porphyrin moieties can readily incorporate transition metal ions that have good binding affinity for nitric oxide. Other planar moieties, such as pyrene, naphthalene, or other macrocycles, can be employed for non-covalent modification of the graphene sheet in a similar fashion to the porphyrin species. These macrocycles can incorporate transition metal ions capable of binding nitric oxide, such as iron. Transition metals known to have particular affinity for nitric oxide are Sc, Ti, V, Cr, Mn, Fe, Co, Ni, Cu, Pb and Zn.

In some embodiments, nitric oxide binding to the modifying layer and/or adsorbing on the graphene surface may cause a change in the local electrostatics (local charge density) and induce a shift in the capacitance of the graphene. The modifying layer may also serve to limit the impact of interfering chemical species on the response of the sensor (limits change in capacitance due to other species).

In some embodiments, the nitric oxide sensor may also include a selectively permeable polymer membrane to enhance selectivity of the sensor toward nitric oxide. This membrane layer may allow for rapid diffusion of nitric oxide to the graphene surface while limiting the diffusion of other analytes.

In some embodiments, the device is an ethanol sensor. The graphene varactor may include a modifying layer capable of selectively interacting with ethanol. The modifying layer may include molecules that are covalently or non-covalently bound to the graphene surface. Examples of these molecules include with good binding affinity for ethanol. In some embodiments, the modifying layer includes a trifluoroacetate moiety.

The trifluoroacetate moiety may include, optionally through a linker, an aryl or heteroaryl group, which may non-covalently bind to the graphene surface via π-stacking interactions. The π-stacking interactions between planar moieties such as pyrene, naphthalene, anthracene or porphyrin and the graphene surface can drive self-assembly of the planar molecules onto the surface of the graphene. For example, pyrene-functionalized trifluoroacetate moiety can be adsorbed to the graphene surface. Different chemical substitution patterns can be used on the periphery of the aryl or heteroaryl group ring, as well as the linker.

In other embodiments, the trifluoroacetate moiety may be covalently bound to the graphene surface. The trifluoroacetate moiety may be bound to the graphene surface by a covalent bond connecting a non-sp2 hybridized carbon on the graphene surface with any suitable attachment point on the trifluoroacetate moiety structure. In some embodiments, the modifying layer is covalently bound to the graphene surface though oxygen atoms on the graphene surface. The minimum number of covalent connections required to keep the modifying layer covalently attached while not disrupting the capacitance of graphene layer may be desirable.

In some embodiments, the modifying layer comprises molecules of Formula (I):

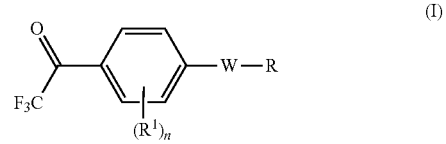

wherein
n is 0, 1, 2, 3 or 4;
R is $C_1$-$C_{20}$alkyl, $C_1$-$C_{20}$alkenyl, aryl, heteroaryl, $C_1$-$C_{20}$alkyl-aryl or $C_1$-$C_{20}$alkyl-heteroaryl, wherein aryl, heteroaryl, $C_1$-$C_{20}$alkyl-aryl and $C_1$-$C_{20}$alkyl-heteroaryl are each optionally substituted with one or more $R^1$, and
$C_1$-$C_{20}$alkyl and $C_1$-$C_{20}$alkenyl are optionally substituted with —O-G, wherein G is the graphene layer;
each $R^1$ is independently —OH, —$NR^2_2$, $C_1$-$C_{10}$alkyl, —$OR^2$ or W—R.
W is a bond, —O—, —N($R^2$)—, —S—, —C(O)—, —C(O)O—, —C(O)N($R^2$)—, —S(O)—, —S(O)$_2$—, —S(O)O— or —S(O)$_2$O—; and
$R^2$ is H, $C_1$-$C_{10}$alkyl, —C(O)—$C_1$-$C_{10}$alkyl, or —$C_1$-$C_{10}$alkyl-aryl.

In some embodiments, R is pyrene, naphthalene, anthracene, or porphyrin optionally substituted with one or more $R^1$ group.

In some embodiments, the modifying layer comprises molecules of Formula (Ia):

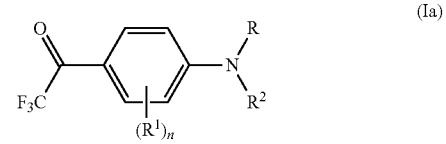

wherein
n is 0, 1, 2, 3 or 4;
R is aryl, heteroaryl, —$C_1$-$C_{20}$alkyl or $C_1$-$C_{20}$alkenyl;
each $R^1$ is independently —OH, —$NR^2_2$, $C_1$-$C_{10}$alkyl, —$OR^2$ or WR; and
$R^2$ is H, $C_1$-$C_{10}$alkyl, —C(O)—$C_1$-$C_{10}$alkyl, or —$C_1$-$C_{10}$alkyl-aryl.

In some embodiments, the modifying layer comprises molecules of Formula (Ib):

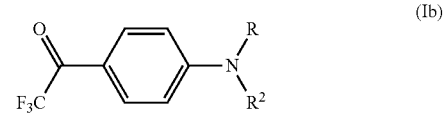

wherein
R is —$C_1$-$C_{20}$alkyl or $C_1$-$C_{20}$alkenyl;
$R^2$ is H, $C_1$-$C_{10}$alkyl, —C(O)—$C_1$-$C_{10}$alkyl, or —$C_1$-$C_{10}$alkyl-aryl.

In other embodiments, the modifying layer comprises molecules of Formula (Ib), wherein R is dodecyl and $R^2$ is —C(O)$CH_3$.

In some embodiments, the modifying layer comprises molecules of Formula (IIc):

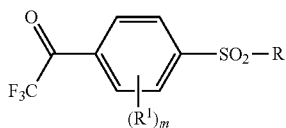

(Ic)

wherein
n is 0, 1, 2, 3 or 4;
R is —$C_1$-$C_{20}$alkyl or $C_1$-$C_{20}$alkenyl;
each $R^1$ is independently —OH, —$NR^2_2$, $C_1$-$C_{10}$alkyl, —$OR^2$ or W—R;
$R^2$ is H, $C_1$-$C_{10}$alkyl, —C(O)—$C_1$-$C_{10}$alkyl, or —$C_1$-$C_{10}$alkyl-aryl.

In other embodiments, the modifying layer comprises molecules of Formula (Ic), wherein n is 0 and R is dodecyl.

In some embodiments, the modifying layer comprises molecules of Formula (IId):

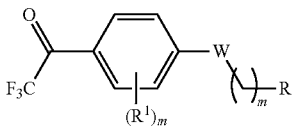

(Id)

wherein
n is 0, 1, 2, 3 or 4;
m is 0, 1, 2, 3, 4, 5, 6, 7, 8, 9 or 10;
R is aryl or heteroaryl;
each $R^1$ is independently —OH, —$NR^2_2$, $C_1$-$C_{10}$alkyl, —$OR^2$ or W—R;
W is a bond, —O—, —$N(R^2)$—, —S—, —C(O)—, —C(O)O—, —C(O)$N(R^2)$—, —S(O)—, —$S(O)_2$—, —S(O)O— or —$S(O)_2$O—; and
$R^2$ is H, $C_1$-$C_{10}$alkyl, —C(O)—$C_1$-$C_{10}$alkyl, or —$C_1$-$C_{10}$alkyl-aryl.

In some embodiments, the modifying layer comprises molecules of Formula (Ie):

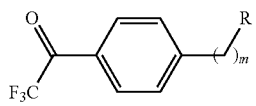

(Ie)

wherein
m is 0, 1, 2, 3, 4, 5, 6, 7, 8, 9 or 10; and
R is aryl or heteroaryl.

In some embodiments, the modifying layer comprises molecules of Formula (Ie), wherein m is 0, 1, 2, 3, 4, 5 or 6, and R is pyrenyl.

In some embodiments, the modifying layer comprises molecules of Formula (I):

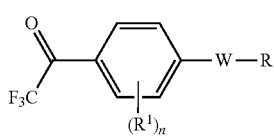

(I)

wherein
n is 0, 1, 2, 3 or 4;
R is $C_1$-$C_{20}$alkyl-O-G, wherein G is the graphene layer;
each $R^1$ is independently —OH, —$NR^2_2$, $C_1$-$C_{10}$alkyl, —$OR^2$ or W—R;
W is a chemical bond, —O—, —$N(R^2)$—, —S—, —C(O)—, —C(O)O—, —C(O)$N(R^2)$—, —S(O)—, —$S(O)_2$—, —S(O)O— or —$S(O)_2$O—; and
$R^2$ is H, $C_1$-$C_{10}$alkyl, —C(O)—$C_1$-$C_{10}$alkyl, or —$C_1$-$C_{10}$alkyl-aryl.

In some embodiments, the modifying layer comprises molecules of Formula (Ia):

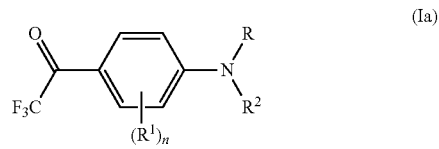

(Ia)

wherein
n is 0, 1, 2, 3 or 4;
each $R^1$ is independently —OH, —$NR^2_2$, $C_1$-$C_{10}$alkyl, —$OR^2$ or W—R; and
$R^2$ is H, $C_1$-$C_{10}$alkyl, —C(O)—$C_1$-$C_{10}$alkyl, or —$C_1$-$C_{10}$alkyl-aryl.

In some embodiments, the modifying layer comprises molecules of Formula (Ib):

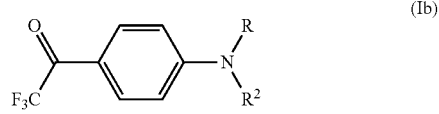

(Ib)

wherein
$R^2$ is H, $C_1$-$C_{10}$alkyl, —C(O)—$C_1$-$C_{10}$alkyl, or —$C_1$-$C_{10}$alkyl-aryl.

In other embodiments, the modifying layer comprises molecules of Formula (Ib), wherein R is dodecyl, and $R^2$ is —$C(O)CH_3$.

In some embodiments, the modifying layer comprises molecules of Formula (Ic):

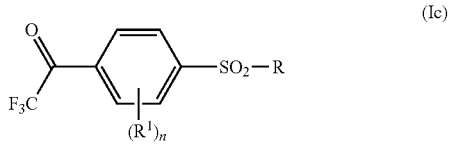

(Ic)

wherein
n is 0, 1, 2, 3 or 4;
each $R^1$ is independently —OH, —$NR^2_2$, $C_1$-$C_{10}$alkyl, —$OR^2$ or W—R;
$R^2$ is H, $C_1$-$C_{10}$alkyl, —C(O)—$C_1$-$C_{10}$alkyl, or —$C_1$-$C_{10}$alkyl-aryl.

In other embodiments, the modifying layer comprises molecules of Formula (Ic), wherein n is 0, and R is dodecyl.

In another aspect, a method for making the modified graphene variable capacitor (varactor) described herein. The method may include:
embedding a gate electrode in a supporting substrate, wherein at least one surface of the gate electrode is not covered by the supporting substrate;

depositing a dielectric layer on the gate electrode, wherein the dielectric layer substantially covers the gate electrode and the supporting substrate;

depositing a graphene layer on the dielectric layer, wherein the graphene layer substantially covers the dielectric layer;

providing a top electrode on the surface of the graphene layer, wherein the top electrode partially covers the surface of the graphene layer; and depositing a modifying layer on the surface of the graphene layer, wherein the modifying layer occupies the surface of the graphene layer not occupied by the top electrode.

In some embodiments, the method further includes the deposition of an insulating layer between the gate electrode and the graphene layer, wherein in the insulating layer substantially covers the gate electrode and the supporting substrate. In other embodiments, the method further includes a permeable membrane, wherein the permeable membrane substantially covers the surface of the modifying layer.

In some embodiments, the deposition is performed by transfer of chemical vapor deposition grown graphene onto the surface of the dielectric. In other embodiments, the deposition is performed using other processes known in the art. The graphene layer may be prepared on a metallic or semiconductor surface and subsequently transferred to the supporting substrate. The transfer step may be completed using various techniques known in the art, such as aqueous flotation, polymer, or thermal tape assisted transfer.) In certain embodiments, the modifying layer is provided by chemical vapor deposition, vacuum deposition, plasma-enhanced chemical vapor deposition, sputtering deposition, and other known techniques for thin film deposition.

In another aspect, a method for measuring the concentration of an analyte in a volume of gas is provided. The method may include:

contacting the device described herein with a volume of gas; and determining the concentration of the analyte in the volume of gas.

In some embodiments, the device may generate raw data following contact with the volume of gas. The raw data may be transferred to a personal electronic device, wherein the personal electronic device may convert the raw data into analyte concentration.

In some embodiments, the method is for the monitoring of a disorder or disease of the upper respiratory track or the lower respiratory track, such as the trachea, bronchi, bronchioles, alveolar sacs as well as the lung parenchyma, interstitial space, and vasculature. In some embodiments the disease is asthma. In other embodiments, the disease is chronic obstructive pulmonary disease (COPD). In other embodiments the disease is cystic fibrosis. In some embodiments, where the analyte is ethanol, the disease may be gastroesophageal reflux disease (Kechagias, S., Jonsson, K.-Å., Franzén, T., Andersson, L., Jones, A. W. Reliability of breath-alcohol analysis in individuals with gastroesophageal reflux disease. *J Forensic Sci* 1999; 44(4): 814-818) or chronic obstructive pulmonary disease (COPD) (Hahn, R. G., Jones, A. W., Billing, B., Stalberg, H. P. *Acta Anaesthesiol Scand.* 1991 July; 35(5): 393-7). Breath-alcohol analysis may also be useful in the determination of blood-glucose levels (Glassetti, P. R., et al. *Diabetes Technology and Therapeutics* 2005, 7, 1, 115-123).

In other embodiments, where the analyte is ethanol, the method may be used for industrial monitoring for ethanol production, which include industrial fermentation processes, biofuel production, and alcoholic beverage production.

In some embodiments, the volume of gas may be provided by human exhalation. Sample collection may involve having a user exhale into the intake port of the device. In some embodiments, sample collection may further include methods for limiting contamination of the sample with nasal nitric oxide. Various methods are available for closing the vellum (soft palate) so that the sample is substantially free of air from the nasopharynx (nasal air). In some embodiments, the user may use a nose clip to block nasal air from mixing with the sample. In other embodiments, the user may employ pursed-lip breathing, which has been shown to not allow air to flow through the nose (Rodenstein, D. O., Stanescu, D.C., *Absence of nasal air flow during pursed lips breathing. The soft palate mechanisms.* Am. Rev. Respir. Dis. 1983 October; 128(4), 716-718).

In embodiments where the analyte is ethanol, the method for measuring the concentration of an analyte in a volume of gas provided by human exhalation further comprises:

determining the blood-alcohol concentration (BAC) of the provider of the exhalation (i.e., the user).

Determination of BAC may be performed by transferring the raw data to a personal electronic device (PED) used in conjunction with the device, wherein the PED may convert the raw data into blood alcohol concentration (BAC). In some embodiments, the user or a third party can be informed of the determined BAC. Further, a BAC limit can be set, and the user or a third party can be alerted if the determined BAC is above the preset level. The user may be informed and/or alerted on the display of the device or on the screen of the PED.

In some embodiments, sample collection occurs over a sample period, and, in some embodiments, the samples may be collected at a location remote from the testing site. The sample period may be a single exhalation or fraction thereof. In some embodiments, the sample period may range from about 1 to about 3 seconds, from about 3 to about 25 seconds, from about to about 10 seconds, from about 10 to about 15 seconds, or about 15 to about 30 seconds. During sampling period, sampling may be repeated at a substantially uniform rate in order to obtain a larger number of data points for determining analyte concentration.

The flow rate of the gas sample may be monitored during the sample period. In some embodiments, the volume of gas may be provided at a substantially consistent flow rate during the sampling period. In other embodiments, the volume of gas may be provided within a flow rate range. The flow rate range may be between about 10 and about 1000 mL/sec, about 10 and about 100 mL/sec, about 100 and about 1000 mL/sec, about 10 and about 75 mL/sec, about 25 and about 100 mL/sec, about 10 and about 50 mL/sec, about 50 and about 150 mL/sec, about 100 and about 250 mL/sec, about 250 and about 1000 mL/sec or about 500 and about 1000 mL/sec. In other embodiments, the flow rate may be inconsistent. When the flow rate is inconsistent, the flow rate may be monitored by a flow rate sensor, which allows for the back-calculation of the analyte concentration based on the monitored flow rate. In this case, the measurements at an arbitrary flow rate may be converted into the equivalent concentration that would be observed at a flow rate of about 50 mL/s. See Am J Respir Crit. Care Med 1997; 155:260-267.

The device may include a flow sensor that optionally informs the user of the volume of gas or the flow rate. In some embodiments, the user may be informed by a visual display. For example, the device may include a display that informs the user of the actual flow rate. In other embodiments, the visual display may be a light (e.g., an LED) that alerts the user when the flow of the gas is outside a desired range. In other embodiments, the user may be alerted by sound. For example, the device may have a component the produces a sound (e.g., a beep) that alerts the user when the flow of the gas is outside a desired range.

In some embodiments, the raw data from the sensor device may be wirelessly transmitted to a personal electronic device (PED) such as a computer, tablet, or smartphone. Software on the PED may convert the raw data that is proportional to the sensor capacitance into an analyte concentration, according to a pre-determined calibration file or function. In embodiments where the volume of gas is the exhaled breath of a human subject using the device (i.e., "a user"), the conversion can provide the concentration of analyte in the user's breath. The results can be displayed to the user and may be saved for future retrieval and tracking of data over time.

In some embodiments, the data obtained on the sensor may be used to inform medical treatment, refine therapeutic strategies, or collect data to aid in diagnosis of respiratory diseases or other conditions for which analyte measured is an indicator. The device may be used to transmit the stored analyte sensing data to a medical user, or to an electronic medical record system to be included in patient records. For example, when the analyte is nitric oxide, diseases associated with high exhaled nitric oxide concentrations include bronchiectasis, viral respiratory tract infections, systemic lupus erythematosus, liver cirrhosis, acute lung allograft rejection, post-transplant bronchiolitis obliterans, and asthma. Diseases associated with low exhaled nitric oxide concentrations include chronic obstructive pulmonary disease (COPD), cystic fibrosis, HIV infection and pulmonary hypertension. Exhaled nitric oxide concentrations may also be correlated to asthma, for diagnosis, monitoring the response to anti-inflammatory medications, to verify adherence to therapy and to predict upcoming asthma exacerbations.

In other embodiments, when the analyte is ethanol, the data obtained by the sensor may be used to activate an ignition interlock system. The ignition interlock system could be present in a vehicle (e.g., a car, train, boat or airplane), equipment (e.g., machinery) or in a mode of access to a location (e.g., a door or gate). For example, when the device determines a blood alcohol level that is above a pre-determined limit, the device may communicate with an automobile ignition system and not allow the automobile to be started. Communication may occur via wireless communication with either a manufacturer installed electronic system or with an after-market interlock systems installed for such a purpose. In some examples, the communication to the interlock occurs through a PED used in conjunction with the device. After the data is transferred from the device to a PED, the PED may transmit information back to the device that indicates whether the BAC is above or below the threshold for disabling the ignition interlock. If the BAC is below the established setpoint, the ignition interlock condition is set to enable the operation of the vehicle or equipment.

What is claimed is:

1. A device for detecting an analyte, comprising:
one or more analyte sensors, each comprising a graphene-based variable capacitor; and
a wireless transmitter,
wherein
the graphene-based variable capacitor comprises a graphene layer and a modifying layer in contact with the graphene layer, wherein the modifying layer comprises molecules having a trifluoroacetate moiety.

2. The device of claim 1, wherein
the modifying layer comprises molecules of Formula (I):

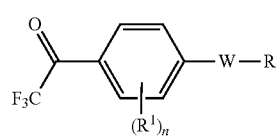

wherein
n is 0, 1, 2, 3 or 4;
R is $C_1$-$C_{20}$alkyl, $C_1$-$C_{20}$alkenyl, aryl, heteroaryl, $C_1$-$C_{20}$alkyl-aryl or $C_1$-$C_{20}$alkyl-heteroaryl, wherein
aryl, heteroaryl, $C_1$-$C_{20}$alkyl-aryl and $C_1$-$C_{20}$alkyl-heteroaryl are each optionally substituted with one or more $R^1$, and
$C_1$-$C_{20}$alkyl and $C_1$-$C_{20}$alkenyl, are each optionally substituted with —O-G, wherein G is the graphene layer;
each $R^1$ is independently —OH, —$NR^2{}_2$, $C_1$-$C_{10}$alkyl, —$OR^2$ or W—R;
W is a bond, —O—, —$N(R^2)$—, —S—, —C(O)—, —C(O)O—, —$C(O)N(R^2)$—, —S(O)—, —$S(O)_2$—, —$S(O)O$— or —$S(O)_2O$—; and
$R^2$ is H, $C_1$-$C_{10}$alkyl, —C(O)—$C_1$-$C_{10}$alkyl, or —$C_1$-$C_{10}$alkyl-aryl.

3. The device of claim 2, wherein
the modifying layer comprises molecules of Formula (Ia):

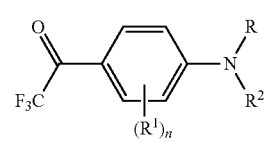

wherein
n is 0, 1, 2, 3 or 4;
R is aryl, heteroaryl, —$C_1$-$C_{20}$alkyl or $C_1$-$C_{20}$alkenyl;
each $R^1$ is independently —OH, —$NR^2{}_2$, $C_1$-$C_{10}$alkyl, —$OR^2$ or WR; and
$R^2$ is H, $C_1$-$C_{10}$alkyl, —C(O)—$C_1$-$C_{10}$alkyl, or —$C_1$-$C_{10}$alkyl-aryl.

4. The device of claim 2, wherein
the modifying layer comprises molecules of Formula (Ib):

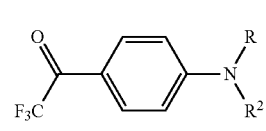

wherein
R is —$C_1$-$C_{20}$alkyl or $C_1$-$C_{20}$alkenyl;
$R^2$ is H, $C_1$-$C_{10}$alkyl, —C(O)—$C_1$-$C_{10}$alkyl, or —$C_1$-$C_{10}$alkyl-aryl.

5. The device of claim 4, wherein
the modifying layer comprises molecules of Formula (Ib), wherein
R is dodecyl; and
$R^2$ is —$C(O)CH_3$.

6. The device of claim 2, wherein
the modifying layer comprises molecules of Formula (Ic):

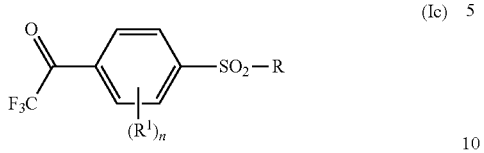

(Ic)

wherein
  n is 0, 1, 2, 3 or 4;
  R is —$C_1$-$C_{20}$alkyl or $C_1$-$C_{20}$alkenyl;
  each $R^1$ is independently —OH, —$NR^2_2$, $C_1$-$C_{10}$alkyl, —$OR^2$ or W—R;
  $R^2$ is H, $C_1$-$C_{10}$alkyl, —C(O)—$C_1$-$C_{10}$alkyl, or —$C_1$-$C_{10}$alkyl-aryl.

7. The device of claim 6, wherein
the modifying layer comprises molecules of Formula (Ic), wherein
  n is 0; and
  R is dodecyl.

8. The device of claim 2, wherein
the modifying layer comprises molecules of Formula (Id):

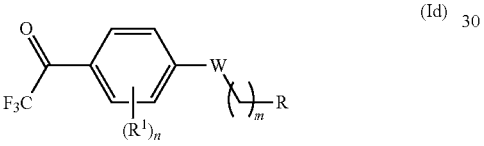

(Id)

wherein
  n is 0, 1, 2, 3 or 4;
  m is 0, 1, 2, 3, 4, 5, 6, 7, 8, 9 or 10;
  R is aryl or heteroaryl;
  each $R^1$ is independently —OH, —$NR^2_2$, $C_1$-$C_{10}$alkyl, —$OR^2$ or W—R;
  W is a bond, —O—, —$N(R^2)$—, —S—, —C(O)—, —C(O)O—, —$C(O)N(R^2)$—, —S(O)—, —$S(O)_2$—, —S(O)O— or —$S(O)_2$O—; and
  $R^2$ is H, $C_1$-$C_{10}$alkyl, —C(O)—$C_1$-$C_{10}$alkyl, or —$C_1$-$C_{10}$alkyl-aryl.

9. The device of claim 2, wherein
the modifying layer comprises molecules of Formula (Ie):

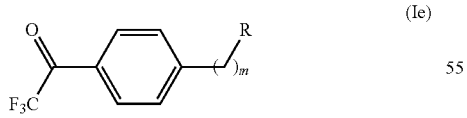

(Ie)

wherein
  m is 0, 1, 2, 3, 4, 5, 6, 7, 8, 9 or 10; and
  R is aryl or heteroaryl.

10. The device of claim 9, wherein
the modifying layer comprises molecules of Formula (Ie), wherein
  m is 0, 1, 2, 3, 4, 5 or 6; and
  R is pyrenyl.

11. The device of claim 2, wherein
the modifying layer comprises molecules of Formula (I):

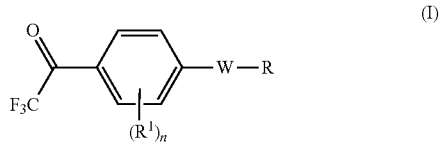

(I)

wherein
  n is 0, 1, 2, 3 or 4;
  R is $C_1$-$C_{20}$alkyl-O-G, wherein G is the graphene layer;
  each $R^1$ is independently —OH, —$NR^2_2$, $C_1$-$C_{10}$alkyl, —$OR^2$ or W—R;
  W is a chemical bond, —O—, —$N(R^2)$—, —S—, —C(O)—, —C(O)O—, —$C(O)N(R^2)$—, —S(O)—, —$S(O)_2$—, —S(O)O— or —$S(O)_2$O—; and
  $R^2$ is H, $C_1$-$C_{10}$alkyl, —C(O)—$C_1$-$C_{10}$alkyl, or —$C_1$-$C_{10}$alkyl-aryl.

12. The device of claim 11, wherein
the modifying layer comprises molecules of Formula (Ia):

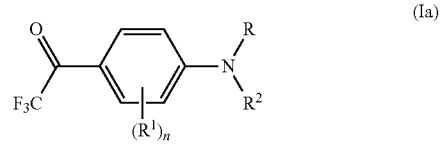

(Ia)

wherein
  n is 0, 1, 2, 3 or 4;
  each $R^1$ is independently —OH, —$NR^2_2$, $C_1$-$C_{10}$alkyl, —$OR^2$ or W—R; and
  $R^2$ is H, $C_1$-$C_{10}$alkyl, —C(O)—$C_1$-$C_{10}$alkyl, or —$C_1$-$C_{10}$alkyl-aryl.

13. The device of claim 11, wherein
the modifying layer comprises molecules of Formula (Ib):

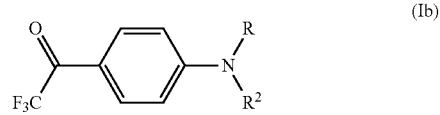

(Ib)

wherein
  $R^2$ is H, $C_1$-$C_{10}$alkyl, —C(O)—$C_1$-$C_{10}$alkyl, or —$C_1$-$C_{10}$alkyl-aryl.

14. The device of claim 13, wherein
the modifying layer comprises molecules of Formula (Ib), wherein
  R is dodecyl-O-G; and
  $R^2$ is —$C(O)CH_3$.

15. The device of claim 11, wherein
the modifying layer comprises molecules of Formula (Ic):

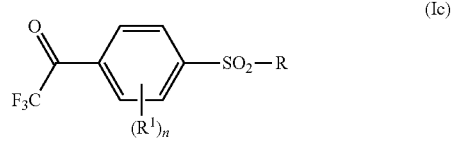

(Ic)

wherein
n is 0, 1, 2, 3 or 4;
each $R^1$ is independently —OH, —$NR^2_2$, $C_1$-$C_{10}$alkyl, —$OR^2$ or W—R;
$R^2$ is H, $C_1$-$C_{10}$alkyl, —C(O)—$C_1$-$C_{10}$alkyl, or —$C_1$-$C_{10}$alkyl-aryl.

16. The device of claim 15, wherein
the modifying layer comprises molecules of Formula (Ic), wherein
n is 0; and
R is dodecyl-O-G.

17. The device of claim 2, wherein
R is $C_1$-$C_{20}$alkyl or $C_1$-$C_{20}$alkenyl, each substituted with —O-G, wherein G is the graphene layer.

18. The device of claim 1, wherein the graphene-based variable capacitor further comprises:
a gate electrode; and
a top electrode.

19. The device of claim 1, wherein
the analyte is ethanol.

20. The device of claim 1, further comprising:
means for providing power to the graphene-based variable capacitor.

* * * * *